United States Patent [19]
Arimori et al.

[11] Patent Number: 6,040,415
[45] Date of Patent: Mar. 21, 2000

[54] BIOCOMPATIBLE POLYMERS

[75] Inventors: Susumu Arimori; Masahiro Seko; Masakazu Tanaka; Noriko Monden; Hideyuki Yokota, all of Otsu, Japan

[73] Assignee: Toyobo Co., Ltd., Osaka, Japan

[21] Appl. No.: 09/147,392

[22] PCT Filed: Apr. 13, 1998

[86] PCT No.: PCT/JP98/01702

§ 371 Date: Dec. 15, 1998

§ 102(e) Date: Dec. 15, 1998

[87] PCT Pub. No.: WO98/46659

PCT Pub. Date: Oct. 22, 1998

[30] Foreign Application Priority Data

Apr. 17, 1997 [JP] Japan .................................. 9-100446
Jun. 30, 1997 [JP] Japan .................................. 9-174549
Dec. 15, 1997 [JP] Japan .................................. 9-345351

[51] Int. Cl.$^7$ .......................... C08G 18/32; C08G 18/38; A61K 31/765; A61K 31/785; A61K 31/80
[52] U.S. Cl. .................... 528/71; 424/78.17; 424/78.27; 424/78.37; 524/27; 525/54.2; 528/72
[58] Field of Search .............................. 424/78.17, 78.27, 424/78.37; 524/27; 525/54.2; 528/71, 72

[56] References Cited

U.S. PATENT DOCUMENTS

| | | | |
|---|---|---|---|
| 5,422,402 | 6/1995 | Bowers et al. | 525/328.2 |
| 5,453,467 | 9/1995 | Bamford et al. | 525/287 |
| 5,591,882 | 1/1997 | Straford et al. | 558/87 |
| 5,599,587 | 2/1997 | Bowers et al. | 427/322 |
| 5,658,561 | 8/1997 | Nakabayashi et al. | 424/78.37 |
| 5,712,326 | 1/1998 | Jones et al. | 523/105 |

FOREIGN PATENT DOCUMENTS

| | | |
|---|---|---|
| 62-500726 | 3/1987 | Japan . |
| 8-134085 | 5/1996 | Japan . |
| 8-259654 | 10/1996 | Japan . |
| 9-235342 | 9/1997 | Japan . |
| 9-241330 | 9/1997 | Japan . |
| WO 86/02933 | 5/1986 | WIPO . |
| WO 87/02684 | 5/1987 | WIPO . |
| WO 88/00956 | 2/1988 | WIPO . |

OTHER PUBLICATIONS

Yamada, M., et al., "Synthesis and Properties of Polyurethanes Containing Phosphatidylcholine Analogues in the Side Chains," Pure Appl. Chem., vol. A32, No. 7, pp. 1235–1242 (1995).
Yamada, M., et al., "Synthesis and Properties of Polymers Containing Phosphatidylcholine Analogues in the Main Chains and Long Alkyl Groups in the Side Chains," Pure Appl. Chem., vol. A32, No. 10, pp. 1723–1733 (1995).
Li, Y., et al., "Novel Blood Compatible Polyurethanes Containing Long-chain Alkyl Groups and Phosphatidylcholine Analogues," Macromol. Chem. Phys., vol. 196, pp. 3143–3153 (1995).
Yamada, M., et al., "Synthesis and Properties of Polyurethanes Containing Phosphatidylcholine Analogues in the Polymer Backbone" Macromol. Rapid Commun., vol. 16, pp. 25–30 (1995).
Li, Y., et al., "Synthesis and Characterization of Polyurethanes Containing Cholesterol and Phosphatidylcholine Analogous Moieties," Macromol. Rapid Commun., vol. 16, pp. 253–258 (1995).
Li, Y., et al., "A new Haemocompatible Phospholipid Polyurethane Based on Hydrogenated Poly-(isoprene) Soft Segment," J. Biomater. Sci. Polymer Edn., vol. 7, No. 10, pp. 893–904 (1996).
Chen, T., et al., "Synthesis and Properties of New Segmented Block Poly(urethane–urea)s Containing Phosphatidylcholine Analogues and Polybutadienes," Macromol. Chem. Phys., vol. 197, pp. 1587–1597 (1996).
Li, Y., et al., "The Effect of Alkyl Chain Length of Amphiphilic Phospholipid Polyurethanes on Haemocompatibilities," Macromol. Chem. Phys., vol. 197, pp. 2827–2835 (1996).
Li, Y., et al., "Synthesis of Comb–Like Polyurethanes Containing Hydrophilic Phosphatidylcholine Analogues in the Main Chains and Hydrophobic Long Chain Alkyl Groups in the Side Chains," Marcromol. Rapid Commun., vol. 17, pp. 737–744 (1995).
Ishihara, K., et al., "Preparation of Phospholipid Polymers and Their Properties as Polymer Hydrogel Membranes," Polymer Journal, vol. 22, No. 5, pp. 355–360 (1990).
Ueda, T., et al., "Preparation of 2–Methacryloyloxyethyl Phosphorylcholine Copolymers with Alkyl Methacrylates and Their Blood Compatibility," Polymer Journal, vol. 24, No. 11, pp. 1259–1269 (1992).

Primary Examiner—Rabon Sergent
Attorney, Agent, or Firm—Foley & Lardner

[57] ABSTRACT

Tpresent invention provide a biocompatible polyurethane or oplyurethane urea containing, in the side chain, phosphorylcholine structure represented by the formula (1)

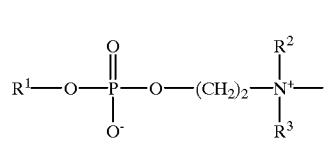

(1)

wherein $R^1$ is $C_{1-20}$ alkyl, $C_{6-12}$ aryl, $C_{7-20}$ aralkyl or a group of the formula:

$R^4-(A)_n-$ (wherein A is $C_{2-10\ oxyalkylene,\ and\ (A)n}$ may be constituted of one kind of oxyalkylene groups or of two or more kinds of oxyalkylene groups linked together in blocks or at random; n is an integer of 1 to 30; and $R^4$ is $C_{1-20}$ alkyl, $C_{6-12}$ aryl or $C_{7-20\ aralkyl)};\ and\ R^2$ and $R^3$ each represent $C_{1-20\ alkyl},\ C_{6-12}$ aryl or $C_{7-20}$ aralkyl and may be the same or different; and an antithrombogenic medical product prepared using the polyurethane or polyurethane urea.

14 Claims, No Drawings

BIOCOMPATIBLE POLYMERS

TECHNICAL FIELD

The present invention relates to biocompatible polyurethanes or polyurethane ureas, in particular polyurethanes or polyurethane ureas which show good antithrombogenicity when employed as medical materials to be brought into direct contact with the living body or constituents of the living body.

BACKGROUND ART

In recent years, high-molecular materials excellent in processability, elasticity and flexibility have been widely used as medical materials. It is expected that such materials will find wider use in artificial organs such as artificial kidneys, artificial lungs, extracorporeal circulation devices and artificial blood vessels, as well as disposable products such as syringes, blood bags and cardiac catheters. Materials of these products for medical use are required to have, in addition to sufficient mechanical strength and durability, biological safety which particularly means a property of not causing coagulation of blood upon contact therewith, i.e., antithrombogenicity.

Conventional methods for imparting antithrombogenicity to medical materials are generally classified into the following three groups:

(1) immobilizing an antithrombogenic mucopolysaccaride (e.g., heparin) or a fibrinolytic activator (e.g., urokinase) on the surface of the material;

(2) modifying the surface of the material so that it carries negative charge or hydrophilicity; and (3) inactivating the surface of the material. The method (1) using heparin (hereinafter referred to as "surface-heparinizing method") is further subdivided into (A) blending of a polymer with heparin, (B) coating of the material surface with an organic solvent-soluble heparin, (C) ionic bonding of heparin to a cationic group in the material, and (D) covalent bonding of the material and heparin.

In the method (1), heparin or urokinase introduced to the material surface exhibits antithrombogenicity or lytic activity on thrombus at the early stage of introduction of the material. In a long-term use, however, the antithrombogenic agents tend to dissolve out, lowering the ability of the material. In other words, according to the methods (A), (B) and (C), a long-term use under physiological conditions generally results in easy release of heparin or the like, making it difficult to achieve sufficient performance of medical materials which are used as implanted in the living body for a long period. The method (D) is beneficial in that the covalently bonded heparin is unlikely to be released, but conventional bonding techniques often alter the conformation of D-glucose or D-gluconic acid constituting heparin, whereby the anticoagulant effect reduces.

The methods (C) and (D) require selection of materials containing a functional group usable for immobilization of heparin, or introduction of such a functional group into the material. Accordingly, these methods narrow the range of usable materials or deteriorate the mechanical strength of the material due to the introduction of the functional group. Moreover, the complicated manipulation may increase the steps necessary for preparing the material.

In the methods (2) and (3), antithrombogenicity can be imparted to the material by introducing a biocompatible functional group. As described above, when an anticoagulating mucopolysaccharide (e.g., heparin) or a fibrinolytic activator (e.g., urokinase) is immobilized on the material, the antithrombogenicity of the material reduces as the antithrombogenic agents dissolve out. It is therefore difficult to retain the antithrombogenicity for a long period. In contrast, a material into which a biocompatible functional group has been introduced can retain the antithrombogenicity during long-term contact with the living body.

Biocompatible functional groups recently actively researched include phosphorylcholine structures. Phosphorylcholine structures are analogous to the structure of a phospholipid forming biomembranes, i.e., phosphatidylcholine. Accordingly, high-molecular materials containing phosphorylcholine structures in the molecule have high affinity to the living body and are useful as antithrombogenic materials.

For example, polymers containing 2-methacryloyloxyethylphosphorylcholine is analogous in structure to phosphatidylcholine, one of the constituents of external walls of cells. When a phospholipid derived from the living body is made to be adsorbed on the polymer, the polymer forms a surface analogous to biomembranes and shows excellent blood compatibility (Japanese Unexamined Patent Publications Nos. 63025/1979 and 96200/1988). It is also reported that high blood compatibility can be achieved by introducing a phosphorylcholine group into the main chain of a polyurethane (Japanese Unexamined Patent Publications Nos. 500726/87, 134085/96 and No. 259654/96 and WO 86/02933). However, the disclosed materials do not have antithrombogenicity sufficient for use as medical materials.

DISCLOSURE OF THE INVENTION

The main object of the invention is to provide a polyurethane or polyurethane urea having excellent biocompatibility.

Another object of the invention is to provide an antithrombogenic polyurethane or polyurethane urea capable of stably exhibiting excellent antithrombo-genicity even in a long-term use.

A further object of the invention is to provide a medical material containing a polyurethane or polyurethane urea having excellent antithrombogenicity.

The present inventors carried out extensive research in view of the above problems, and found that a polyurethane or polyurethane urea with a specific structure containing specific phosphorylcholine group in the side chain can achieve the above objects. Further, they found that when quaternary ammonium group is introduced into part of the polyurethane or polyurethane urea with a specific structure using a diol component containing quaternary ammonium group and then a mucopolysaccaride is introduced into the polyurethane or polyurethane urea by electrostatic interaction between the ammonium cation and anion of the mucopolysaccharide, a particularly improved antithrombogenicity is achieved at the early stage of contact with constituents of the living body, and the excellent antithrombogenicity can be stably exhibited not only at the early stage but also after a long-term contact. The present invention has been accomplished based on the above findings.

The present invention provides the following biocompatible polyurethanes or polyurethane ureas, antithrombogenic coating materials, materials for antithrombogenic medical products, and antithrombogenic medical products.

1. A biocompatible polyurethane or polyurethane urea containing, in the side chain, phosphorylcholine structure represented by the formula (1):

$$R^1-O-\underset{O^-}{\underset{|}{\overset{O}{\overset{\|}{P}}}}-O-(CH_2)_2-\underset{R^3}{\overset{R^2}{\overset{|}{N^+}}}- \qquad (1)$$

wherein $R^1$ is $C_{1-20}$ alkyl, $C_{6-12}$ aryl, $C_{7-20}$ aralkyl or a group of the formula:

$$R^4-(A)_n-$$

(wherein A is $C_{2-10}$ oxyalkylene, and $(A)_n$ may be constituted of one kind of oxyalkylene groups or of two or more kinds of oxyalkylene groups linked together in blocks or at random; n is an integer of 1 to 30; and $R^4$ is $C_{1-20}$ alkyl, $C_{6-12}$ aryl or $C_{7-20}$ aralkyl); and $R^2$ and $R^3$ each represent $C_{1-20}$ alkyl, $C_{6-12}$ aryl or $C_{7-20}$ aralkyl and may be the same or different.

2. A polyurethane or polyurethane urea according to item 1 containing, per 1.0 g of the polymer, 0.03 to 3.00 mmol of phosphorus in the phosphorylcholine structure represented by the formula (1).

3. A polyurethane or polyurethane urea according to item 1 obtainable by reacting:

(A) active hydrogen-containing compounds which are:

(i) 0.1 to 50 mol % of a diol containing phosphorylcholine structure represented by the formula (1):

$$R^1-O-\underset{O^-}{\underset{|}{\overset{O}{\overset{\|}{P}}}}-O-(CH_2)_2-\underset{R^3}{\overset{R^2}{\overset{|}{N^+}}}- \qquad (1)$$

wherein $R^1$ is $C_{1-20}$ alkyl, $C_{6-12}$ aryl, $C_{7-20}$ aralkyl or a group of the formula:

$$R^4-(A)_n-$$

(wherein A is $C_{2-10}$ oxyalkylene, and $(A)_n$ may be constituted of one kind of oxyalkylene groups or of two or more kinds of oxyalkylene groups linked together in blocks or at random; n is an integer of 1 to 30; and $R^4$ is $C_{1-20}$ alkyl, $C_{6-12}$ aryl or $C_{7-20}$ aralkyl); and $R^2$ and $R^3$ each represent $C_{1-20}$ alkyl, $C_{6-20}$ aryl, or $C_{7-20}$ aralkyl and may be the same or different;

(ii) 1 to 40 mol % of a polymer diol;
(iii) 1 to 90 mol % of a chain extender; and
(iv) 30 mol % or less of other active hydrogen-containing compound; the combined amount of the compounds (i) to
(iv) being 100 mol %; and
(B) diisocyanate compound.

4. A polyurethane or polyurethane urea according to item 3 wherein the diol containing phosphorylcholine structure represented by the formula (1) is at least one member selected from the compounds represented by the formulas (2) and (3):

$$R^2-\overset{R^3}{\overset{|}{N^+}}-(CH_2)_2-O-\underset{O}{\underset{\|}{\overset{O^-}{\overset{|}{P}}}}-O-R^1 \qquad (2)$$
$$(CH_2)_m$$
$$HO-R^5-\underset{}{\overset{}{N}}-R^6-OH$$

$$R^2-\overset{R^3}{\overset{|}{N^+}}-(CH_2)_2-O-\underset{O}{\underset{\|}{\overset{O^-}{\overset{|}{P}}}}-O-R^1 \qquad (3)$$
$$(CH_2)_m$$
$$HO-R^5-\underset{R^7}{\overset{}{\overset{|}{C}}}-R^6-OH$$

wherein $R^1$ is $C_{1-20}$ alkyl, $C_{6-12}$ aryl, $C_{7-20}$ aralkyl or a group of the formula:

$$R^4-(A)_n-$$

(wherein A is $C_{2-10}$ oxyalkylene, and $(A)_n$ may be constituted of one kind of oxyalkylene groups or of two or more kinds of oxyalkylene groups linked together in blocks or at random; n is an integer of 1 to 30; and $R^4$ is $C_{1-20}$ alkyl, $C_{6-12}$ aryl or $C_{7-20}$ aralkyl); $R^2$ and $R^3$ each represent $C_{1-20}$ alkyl, $C_{6-12}$ aryl or $C_{7-20}$ aralkyl and may be the same or different; $R^5$ and $R^6$ each represent $C_{1-10}$ alkylene and may be the same or different; m is an integer of 1 to 10; and $R^7$ in the formula (3) is a hydrogen atom, $C_{1-20}$ alkyl, $C_{6-12}$ aryl or $C_{7-20}$ aralkyl.

5. A polyurethane or polyurethane urea according to item 1, containing, in the side chain, quaternary ammonium group represented by the formula (4):

$$-\underset{R^{10}}{\overset{R^8}{\overset{|}{N^+}}}-R^9 \cdot X^- \qquad (4)$$

wherein $R^8$, $R^9$ and $R^{10}$ each represent $C_{1-20}$ alkyl, $C_{6-12}$ aryl or $C_{7-20}$ aralkyl and may be the same or different, and any one of $R^8$, $R^9$ and $R^{10}$ may be a hydrogen atom; and X is an anionic group or an anionic compound;

or containing, in the main chain, quaternary ammonium group represented by the formula (5):

$$-\underset{R^9}{\overset{R^8}{\overset{|}{N^+}}}- \quad \cdot X^- \qquad (5)$$

wherein $R^8$ and $R^9$ each represent $C_{1-20}$ alkyl, $C_{6-12}$ aryl or $C_{7-20}$ aralkyl and may be the same or different, and either one of $R^8$ and $R^9$ may be a hydrogen atom; and X is an anionic group or an anionic compound.

6. A polyurethane or polyurethane urea according to item 3 wherein at least one member selected from the diols containing quaternary ammonium group and represented by the formulas (6) to (8) is used as part or whole of (iv) the other active hydrogen-containing compound, the proportion of the diol being 0.1 mol % or more per 100 mol % of the combined amount of the active hydrogen-containing compounds:

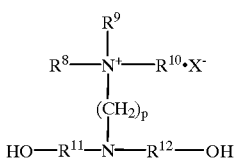

(6)

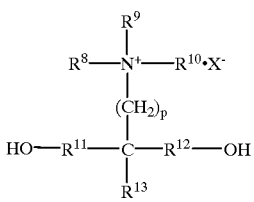

(7)

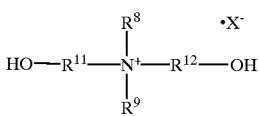

(8)

wherein $R^8$, $R^9$ and $R^{10}$ each represent $C_{1-20}$ alkyl, $C_{6-12}$ aryl or $C_{7-20}$ aralkyl and may be the same or different, and any one of $R^8$, $R^9$ and $R^{10}$ may be a hydrogen atom; X is an anionic group or an anionic compound; $R^{11}$ and $R^{12}$ each represent $C_{1-10}$ alkylene and may be the same or different; $R^{13}$ is $C_{1-20}$ alkyl, $C_{6-12}$ aryl or $C_{7-20}$ aralkyl; and p is an integer of 2 to 10.

7. A polyurethane or polyurethane urea according to any one of items 1 to 6 having a weight-average molecular weight of 3,000 to 8,000,000.

8. A polyurethane or polyurethane urea according to item 5 or 6 wherein at least part of the ammonium groups forms ionic complex with mucopolysaccharide.

9. A polyurethane or polyurethane urea according to item 8 wherein the mucopolysaccharide is heparin.

10. An antithrombogenic coating material comprising a polyurethane or polyurethane urea according to any one of items 1 to 9 as dissolved in an organic solvent.

11. An antithrombogenic material for medical products containing a polyurethane or polyurethane urea according to any one of items 1 to 9 as an active ingredient.

12. An antithrombogenic medical product having a coating layer formed from an antithrombogenic coating material according to item 10.

13. An antithrombogenic medical product prepared using an antithrombogenic material according to item 11.

The polyurethane or polyurethane urea (hereinafter sometimes collectively referred to as "polyurethane polymer") of the invention contains, in the side chain, phosphorylcholine structure represented by the formula (1):

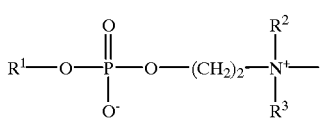

(1)

wherein $R^1$ is $C_{1-20}$ alkyl, $C_{6-12}$ aryl, $C_{7-20}$ aralkyl or a group of the formula:

(wherein A is $C_{2-10}$ oxyalkylene, and $(A)_n$ may be constituted of one kind of oxyalkylene groups or of two or more kinds of oxyalkylene groups linked together in blocks or at random; n is an integer of 1 to 30; and $R^4$ is $C_{1-20}$ alkyl, $C_{6-12}$ aryl or $C_{7-20}$ aralkyl); and $R^2$ and $R^3$ each represent $C_{1-20}$ alkyl, $C_{6-12}$ aryl or $C_{7-20}$ aralkyl and may be the same or different.

As the result of introducing phosphorylcholine, which is analogous in structure to phosphatidylcholine constituting biomembranes, into the side chain of the polyurethane polymer of the invention, the polyurethane polymer of the invention has improved biocompatibility and can exhibit remarkably excellent antithrombogenity, as compared with polyurethanes having phosphorylcholine in the main chain. The result can be achieved presumably for the following reason. While a functional group present in the main chain is generally difficult to fully exhibit its properties owing to the entangled structure of the main chain, a functional group present in the side chain has improved motility and fully exhibits its properties because the motion of the functional group is not suppressed by the high-molecular main chain. That is, the polyurethane polymer of the invention shows good biocompatiblity and excellent antithrombogenicity presumably because the phosphorylcholine, which has been introduced to the side chain, has improved motility and therefore fully exhibits the effect of the structure analogous to biomembranes.

In addition to the phosphorylcholine structures of the formula (1) in the side chain, the polyurethane polymer of the invention may contain, in the side chain, quaternary ammonium group represented by the formula (4):

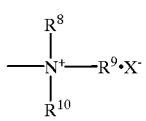

(4)

wherein $R^8$, and $R^9$ and $R^{10}$ each represent $C_{1-20}$ alkyl, $C_{6-12}$ aryl or $C_{7-20}$ aralkyl and may be the same or different, and any one of $R^8$, $R^9$ and $R^{10}$ may be a hydrogen atom; and X is an anionic group or an anionic compound;

or may contain, in the main chain, quaternary ammonium group represented by the formula (5):

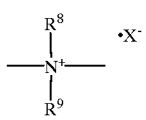

(5)

wherein $R^8$ and $R^{10}$ each represent $C_{1-20}$ alkyl, $C_{6-12}$ aryl or $C_{7-20}$ aralkyl and may be the same or different, and either one of $R^8$ and $R^9$ may be a hydrogen atom; and X is an anionic group or an anionic compound. In both cases, an antithrombogenic mucopolysaccharide can be introduced into the polyurethane polymer by the electrostatic interaction between the ammonium cation and anion of the mucopolysaccharide. As the result, a material having a surface comprising the quaternary ammonium-containing polyurethane polymer has more improved antithrombogenicity at the early stage of contact with the living body or constituents of the living body, because the antithrombogenic mucopolysaccharide acts effectively. Even if the mucopolysaccharide should dissolve out in a long-term use, the phosphorylcholine structure effectively serves to maintain the good antithrombogenicity. Accordingly, the material stably shows good antithrombogenicity from the early stage of contact over a prolonged period of contact. The polyurethane polymer of the invention may have either one or both of the quaternary ammonium groups of the formulas (4) and (5) in the molecule.

As used herein, the $C_{1-20}$ alkyl means straight- or branched-chain alkyl, or cycloalkyl. Specific examples of the $C_{1-20}$ alkyl include methyl, ethyl, propyl, isopropyl, butyl, tert-butyl, pentyl, hexyl and cyclohexyl. The $C_{6-12}$ aryl is substituted or unsubstituted phenyl or naphtyl which may have 1 to 3 substituents selected from methyl, ethyl, butyl, methoxy, ethoxy and the like. Specific examples of the $C_{6-12}$ aryl include phenyl, tolyl and xylyl. Examples of the $C_{7-20}$ aralkyl include benzyl, phenethyl, phenylbutyl, diphenylmethyl, triphenylmethyl, naphtylmethyl and naphtylethyl. The $C_{2-10}$ alkylene means straight- or branched-chain alkylene. Specific examples of the $C_{2-10}$ alkylene include ethylene, propylene, butylene, pentamethylene, hexamethylene, isopropylene and 2-methylhexamethylene.

The polyurethane polymer of the present invention can be obtained by reacting active hydrogen-containing compound with diisocyanate compound.

Monomer components for use in preparation of the polyurethane polymer of the invention are described below.

Active Hydrogen-containing Compound

Usable active hydrogen-containing compounds include diols containing phosphorylcholine structure represented by the formula (1). Other diols and/or diamines can be also used as required. The active hydrogen-containing compounds are not limited and can be suitably selected from compounds containing active hydrogen reactive with isocyanate. For obtaining a polyurethane polymer having high mechanical strength and good durability as well as good biocompatiblity, the following active hydrogen-containing compounds are preferably used in combination.

(i) A diol containing phosphorylcholine structure represented by the formula (1):

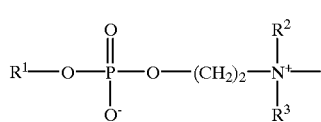

(1)

wherein $R^1$, $R^2$ and $R^3$ are as defined above, (ii) a polymer diol, (iii) a chain extender, and, where necessary, (iv) other active hydrogen-containing compound.

Following is description of the these compounds.

(i) Diol Containing Phosphorylcholine Structure

Of the above active hydrogen-containing compounds, (i) the diol containing phosphorylcholine structure of the formula (1) is not limited insofar as it contains phosphorylcholine structure of the formula (1). Preferred are diols wherein a group of the formula $-(CH_2)_m-$ (wherein m is an integer of 1 to 10) is bonded to the nitrogen atom in the formula (1). Examples of such diols are those represented by the formulas (2) and (3):

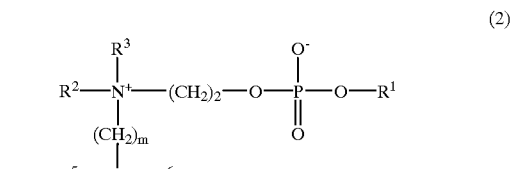

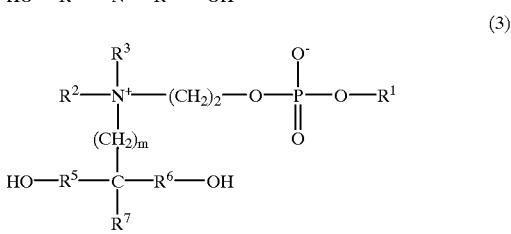

In the formulas (2) and (3), $R^1$ is $C_{1-20}$ alkyl, $C_{6-12}$ aryl, $C_{7-20}$ aralkyl or a group of the formula:

$$R^4-(A)_n-$$

(wherein A is $C_{2-10}$ oxyalkylene, and $(A)_n$ may be constituted of one kind of oxyalkylene groups or of two or more kinds of oxyalkylene groups linked together in blocks or at random; specific examples of the $C_{2-10}$ oxyalkylene being oxyethylene, oxypropylene, oxybutylene, oxypentamethylene, oxyhexamethylene or the like; n is an integer of 1 to 30, preferably 3 to 15, more preferably 3 to 10; and $R^4$ is $C_{1-20}$ alkyl, $C_{6-12}$ aryl or $C_{7-20}$ aralkyl); $R^2$ and $R^3$ each represent $C_{1-20}$ alkyl, $C_{6-12}$ aryl or $C_{7-20}$ aralkyl, and may be the same or different; $R^5$ and $R^6$ each represent $C_{1-10}$ alkylene, and may be the same or different; and m is an integer of 1 to 10, preferably 1 to 7. In the formula (3), $R^7$ is a hydrogen atom, $C_{1-20}$ alkyl, $C_{6-12}$ aryl or $C_{7-20}$ aralkyl.

Of the compounds represented by the formulas (2) and (3), preferred examples are the following.

Compounds of the formula (2) wherein $R^2=R^3=$methyl, $R^5=R^6=-CH_2-CH(CH_3)-$, m=3, and $R^1=$methyl, ethyl, propyl, isopropyl, butyl, tert-butyl, hexyl, cyclohexyl, octyl or the like.

Compounds of the formula (2) wherein $R^2=R^3=$methyl, $R^5=R^6=-CH_2-CH(CH_3)-$, m=3 and $R^1=R^4-(A)_n-$ [wherein $R^4=$methyl, ethylene, propyl, butyl, octyl, lauryl, cetyl or oleyl, A=oxyethylene (n=3–20), oxypropylene (n is, for example, 3–20), oxybutylene (n is, for example, 3–20), oxyhexamethylene (n is, for example, 3–20), an oxyethylene-oxypropylene copolymer (n is, for example, 3–20) or the like].

Compounds of the formula (3) wherein $R^2=R^3=R^7=$methyl, $R^5=R^6=$methylene, m=1, and $R^1=$methyl, ethyl, propyl, isopropyl, butyl, tert-butyl, hexyl, cyclohexyl, octyl or the like.

Compounds of the formula (3) wherein $R^2=R^3=R^7=$methyl, $R^5=R^6=$methylene, m=1 and $R^1=R^4-(A)_n-$ [wherein $R^4=$methyl, ethylene, propyl, butyl, octyl, lauryl, cetyl or oleyl and A=oxyethylene (n=3–20), oxypropylene (n is, for example, 3–20), oxybutylene (n is, for example, 3–20), oxyhexamethylene (n is, for example, 3–20), an oxyethylene-oxypropylene copolymer (n is, for example, 3–20) or the like].

Of the compounds of the formulas (2) and (3), those wherein $R^1$ is a group of the formula $R^4-(A)_n-$ improve the hydrophilicity of the material and make the material more biocompatible, because of the presence of the hydrophilic polyoxyalkylene group at the end of the side chain. The inhibitory effects on blood coagulation factor activity and on platelet adhesion are improved synergetically by the effect of such a hydrophilic group and the improved motility of the phosphorylcholine owing to the presence of the phosphorylcholine in the side chain.

The compounds of the formulas (2) and (3) can be produced, for example, by the method illustrated by the following reaction schema.

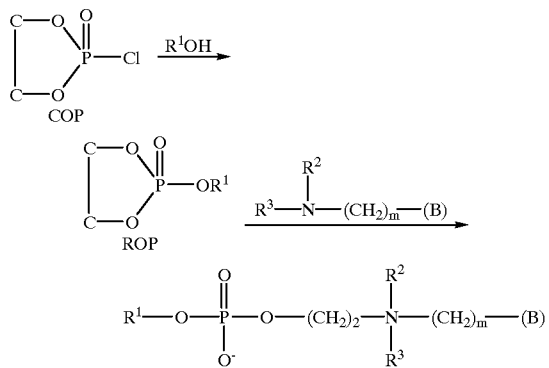

In the above reaction schema, $R^1$, $R^2$, $R^3$ and m are as defined above, and —(B) represents a group of the following formula (I) or (II):

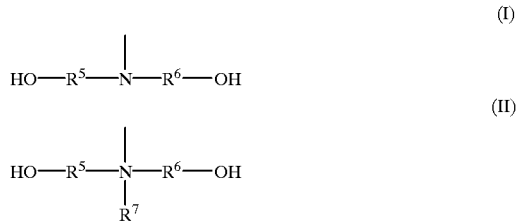

In the formulas (I) and (II), $R^5$, $R^6$ and $R^3$ are as defined above.

The method according to the above reaction schema is carried out as follows, using a known compound, 2-chloro-2-oxo-1,3,2-dioxaphosphorane (COP), as the starting material. First, according to the method described in Makromol. Chem., Rapid. Commun., 3, 457 (1982), a solution of COP in tetrahydrofuran (THF) is slowly added dropwise to a THF solution of $R^1OH$ and triethylamine in a nitrogen stream at a low temperature ranging from about −30 to −10° C. After completion of addition, the mixture is reacted in a nitrogen stream at −10° C. or lower for about 3 to 5 hours. Thereafter, the precipitate (triethylamine hydrochloride) is filtered off, the filtrate is evaporated in vacuo, and the residue is dried in vacuo to give 2-R-yloxy-2-oxo-1,3,2-dioxaphosphoran (ROP).

Subsequently, according to the method described in J. Macromol. Sci. —Pure Appl. Chem., A32, 1235 (1995), equimolar amounts of the obtained ROP and a tertiary amine-containing diol are dissolved in dry acetonitrile, followed by a reaction in a sealed reactor at about 50 to 100° C. for about 12 to 72 hours. After completion of reaction, the solvent is evaporated in vacuo, and the residue is washed several times with cyclohexane to obtain the desired compound of the formula (2) or (3).

(ii) Polymer Diol

Usable polymer diols include polyoxyalkylene glycol, polycarbonate diol, polyester diol, polybutadiene diol, polyisoprene diol and hydrogenated polyisoprene diol. Among them, polyoxyalkylene glycol is a compound wherein hydroxyl groups are bonded to both ends of polyoxyalkylene comprising straight- or branched-chain alkylene groups having 2 to 8, preferably about 2 to 6 carbon atoms, such as ethylene, tetraethylene, hexamethylene or the like, bonded to each other by ether linkage.

The polymer diol for use in the invention preferably has a monomer repeating unit number of about 4 to 200, more preferably about 10 to 150. Use of such polymer diol imparts suitable flexibility to the resulting polyurethane.

(iii) Chain Extender

At least one member selected from alkylenediols and alkylenediamines can be used as the chain extender.

Preferred alkylenediols are those having hydroxyl groups at both ends of a straight- or branched-chain alkylene having about 2 to 8, preferably about 2 to 6 carbon atoms. Specific examples of useful alkylenediols include ethylene glycol, propylene glycol, butylene glycol, 1,6-hexanediol, neopentyl glycol and like alkylene glycols.

Examples of useful alkylenediamines include ethylenediamine, propylenediamine, butylenediamine, hexamethylenediamine and like straight-chain alkylenediamines; 1,2-diaminopropane, 1,3-diaminopentane and like branched-chain alkylenediamines; and 1,2-cyclohexanediamine, 1,3-cyclohexanediamine, 1,4-cyclohexanediamine and like cyclic alkylenediamines.

As the chain extender, the above alkylenediols and alkylenediamines can be used either singly or in combination. Use of the chain extender imparts suitable hardness to the resulting polyurethane.

(iv) Other Active Hydrogen-containing Compound

According to the invention, diols and/or diamines other than the above compounds (i) to (iii) can be used as the other active hydrogen-containing compound.

The other active hydrogen-containing compound is not limited and may be suitably selected from diols and/or diamines according to required properties. They can be used singly or in combination.

Diols and/or diamines having a functional group other than phosphorylcholine structure can be used. Examples of other functional groups include a hydroxyl group for imparting hydrophilicity to the material; a carboxyl group, sulfonic acid group for negatively charging the material; and a diazo group, azide group for improving photoreactivity of the material. Diols and diamines having these functional groups can be suitably selected from those known.

A polyurethane polymer containing, in the side chain, quaternary ammonium group of the formula (4):

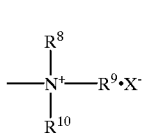

(4)

wherein $R^8$, $R^9$, $R^{10}$ and X are as defined above, or containing, in the main chain, quaternary ammonium group of the formula (5):

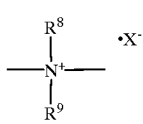

(5)

wherein $R^8$, $R^9$ and X are as defined above, can be obtained using, as the other active hydrogen-containing compound, at least one member selected from the diols having quaternary ammonium group and represented by the formulas (6) to (8):

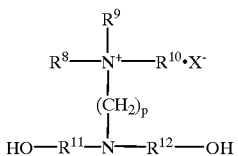
(6)

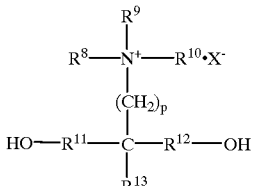
(7)

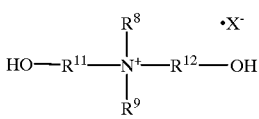
(8)

In the formulas (6) to (8), $R^8$, $R^9$ and $R^{10}$ are as defined above; $R^{11}$ and $R^{12}$ each represent $C_{1-10}$ alkylene and may be the same or different; $R^{13}$ is $C_{1-20}$ alkyl, $C_{6-12}$ aryl or $C_{7-20}$ aralkyl; and p is an integer of 2 to 10.

X is not limited and may be any anionic group or anionic compound. Preferred are, for example, chloride ion or other halide ions, paratoluenesulfonate anion, acetate ion, trifluoroacetate ion, perchlorate ion, etc.

Diols containing quaternary ammonium group can be obtained by, for example, dissolving or dispersing a corresponding tertiary amine in an organic solvent, adding a quaternizing agent, distilling off the solvent, washing the residue to remove impurities, and purifying the resulting quaternary ammonium diol by recrystallization or like method.

Among the diols containing quaternary ammonium group of the formulas (6) to (8), the following compounds are preferred.

Compounds of the formula (6) wherein $R^8=R^9$=methyl, $R^{11}=R^{12}$=—$CH_2$—$CH(CH_3)$—, p=3, $R^{10}$=a hydrogen atom, methyl, ethyl, propyl, isopropyl, butyl, tert-butyl, hexyl, cyclohexyl, octyl, lauryl, myristyl, cetyl or stearyl, and $X^-$ is a fluoride ion, chloride ion, bromide ion, iodide ion, paratoluenesulfonate ion, perchlorate ion, acetate ion, trifluoroacetate ion or the like.

Compounds of the formula (6) wherein $R^8=R^9$=ethyl, $R^{11}=R^{12}$=—$CH_2$—$CH(CH_3)$—, p=3, $R^{10}$=a hydrogen atom, methyl, ethyl, propyl, isopropyl, butyl, tert-butyl, hexyl, cyclohexyl, octyl, lauryl, myristyl, cetyl or stearyl, and $X^-$ is a fluoride ion, chloride ion, bromide ion, iodide ion, paratoluenesulfonate ion, perchlorate ion, acetate ion, trifluoroacetate ion or the like.

Compounds of the formula (7) wherein $R^8=R^9=R^{13}$=methyl, $R^{11}=R^{12}$=methylene, p=1, $R^{10}$=a hydrogen atom, methyl, ethyl, propyl, isopropyl, butyl, tert-butyl, hexyl, cyclohexyl, octyl, lauryl, myristyl, cetyl or stearyl, and $X^-$ is a fluoride ion, chloride ion, bromide ion, iodide ion, paratoluenesulfonate ion, perchlorate ion, acetate ion, trifluoroacetate or the like.

Compounds of the formula (7) wherein $R^8=R^9=R^{13}$=ethyl, $R^{11}=R^{12}$=methylene, p=1, $R^{10}$=a hydrogen atom, methyl, ethyl, propyl, isopropyl, butyl, tert-butyl, hexyl, cyclohexyl, octyl, lauryl, myristyl, cetyl or stearyl, and $X^-$ is a fluoride ion, chloride ion, bromide ion, iodide ion, paratoluenesulfonate ion, perchlorate ion, acetate ion, trifluoroacetate ion or the like.

Compounds of the formula (7) wherein $R^8=R^9$=ethyl, $R^{11}=R^{12}$=methylene, $R^{13}$=a hydrogen atom, p=1, $R^{10}$=hydrogen atom, methyl, ethyl, propyl, isopropyl, butyl, tert-butyl, hexyl, cyclohexyl, octyl, lauryl, myristyl, cetyl or stearyl, and $X^-$ is a fluoride ion, chloride ion, bromide ion, iodide ion, paratoluenesulfonate ion, perchlorate ion, acetate ion, trifluoroacetate ion or the like.

Compounds of the formula (8) wherein $R^8$=methyl, $R^{11}=R^{12}$=ethylene, $R^9$=a hydrogen atom, methyl, ethyl, propyl, isopropyl, butyl, tert-butyl, hexyl, cyclohexyl, octyl, lauryl, myristyl, cetyl or stearyl, and $X^-$ is a fluoride ion, chloride ion, bromide ion, iodide ion, paratoluenesulfonate ion, perchlorate ion, acetate ion, trifluoroacetate ion or the like.

Compounds of the formula (8) wherein $R^8$=ethyl, $R^{11}=R^{12}$=ethylene, $R^9$=a hydrogen atom, methyl, ethyl, propyl, isopropyl, butyl, tert-butyl, hexyl, cyclohexyl, octyl, lauryl, myristyl, cetyl or stearyl, and $X^-$ is a fluoride ion, chloride ion, bromide ion, iodide ion, paratoluenesulfonate ion, perchlorate ion, acetate ion, trifluoroacetate ion or the like.

These compounds may be used singly or in combination.

(iv) Proportions of Active Hydrogen-containing Compounds

The proportions of the active hydrogen-containing compounds are not limited, but preferred proportions are (i) 0.1 to 50 mol % of a diol containing phosphorylcholine structure of the formula (1), (ii) 1 to 40 mole % of a polymer diol, (iii) 1 to 90 mol % of a chain extender, and (iv) 30 mol % or less of other active hydrogen-containing compound, per 100 mol % of the combined amount of the active hydrogen-containing compounds. Use of the compounds in the above proportions makes it possible to obtain a polyurethane polymer having high mechanical strength and good durability, as well as excellent biocompatiblity.

For introducing quaternary ammonium group of the formula (4) or (5) into the polyurethane in order to form ionic complex with mucopolysaccharide, at least one member selected from the diols having quaternary ammonium group and represented by the formulas (6) to (8) is used preferably in a proportion of 0.1 mol % or more per 100 mol % of the combined amount of the active hydrogen-containing compounds. The diol having quaternary ammonium group is used as part or whole of (iv) the other active hydrogen-containing compound. Such a diol is preferably used in a proportion up to 30 mol %. When an active hydrogen-containing compound other than the quaternary ammonium-containing diol is used as (iv) the other active hydrogen-containing compound, the combined amount of (iv) the other active hydrogen-containing compounds including the quaternary ammonium-containing diol is preferably 30 mol % or less.

Diisocyanate Compound

The diisocyanate compound for use in the invention is not limited. Any of diisocyanates conventionally used in preparation of polyurethanes or diisocyanates which will be developed in the future can be used as suitably selected according to desired properties. Specific examples of diisocyanate compounds include ethylene diisocyanate, trimethylene diisocyanate, tetramethylene diisocyanate, pentamethylene diisocyanate, octamethylene diisocyanate, undecamethylene diisocyanate, dodecamethylene diisocyanate, cyclopentylene-1,3-diisocyanate, cyclohexane-1,4-diisocyanate, 4,4'-methylenebis (cyclohexylisocyanate), isophorone diisocyanate and like aliphatic diisocyanates; and 2,4-tolylene diisocyanate, 2,6- tolylene diisocyanate, mixtures of 2,4-tolylene diisocyanate and 2,6-tolylene diisocyanate, xylylene-1,4-diisocyanate, 4,4'-diphenylmethane diisocyanate, 4,4'-diphenylpropane diisocyanate, 4-isocyanate benzyl isocyanate, m-phenylene diisocyanate, p-phenylene diisocyanate, naphthalene-1,4-diisocyanate, naphthalene-1,5-diisocyanate and like aromatic diisocyanates.

Polyurethane or Polyurethane Urea

The method for preparing the polyurethane or polyurethane urea (collectively "polyurethane polymer") of the invention is not limited. The polyurethane polymer of the invention can be prepared in conventional manners, by reacting the active hydrogen-containing compound and the diisocyanate compound in an organic solvent. Usable organic solvents are, for example, hexamethylphosphoric triamide (HMPA), N-methylpyrrolidone (NMP), N-methylformamide (NMF), N,N-dimethylformamide (DMF), N,N-dimethylacetoamide (DMAc), tetrahydrofuran (THF), toluene, dioxane, etc. These organic solvents can be used as a mixture. The ratio of the active hydrogen-containing compound to the diisocyanate compound for the reaction is about 0.7 to 1.5 equivalents, preferably about 0.8–1.2 equivalents of the active hydrogen-containing compound to 1 equivalent of the diisocyanate compound.

Specific reaction conditions vary according to the structures of the diisocyanates and diols used, but the reaction can be carried out, for example, in a nitrogen atmosphere at about 20 to 150° C. for 1 to 50 hours with stirring. The reaction product is purified by, for example, reprecipitation.

The polyurethane urea of the invention can be prepared also by reacting the diol components, i.e., the diol of the formula (2) or (3) containing phosphorylcholine structure, polymer diol, alkylene diol and the like, with the diisocyanate compound by the above method to obtain a prepolymer having isocyanate groups at the end, dissolving the prepolymer in HMPA, NMP, NMF, DMF, DMAc, THF or like organic solvent, cooling the solution and adding alkylene diamine to extend the chain.

For the polymerization to obtain the polyurethane polymer, dibutyltin dilaurate, tetrabuthoxy titanium or like polymerization catalyst may be added so that the polymerization efficiently proceeds. The amount of the polymerization catalyst added is usually about 10 to 1000 ppm based on the total amount of the reaction mixture.

The polyurethane polymer of the invention has a weight-average molecular weight of about 3,000 to 8,000,000, preferably about 5,000 to 5,000,000. Molecular weights as used herein are values measured at 50° C. by gel permeation chromatography (GPC) carried out using four gel columns, i.e., Shodex AD-803/S, AD-804/S, AD-806/S and KD-802 connected in series, a 0.1% lithium bromide solution in DMF as the moving phase, and a calibration curve determined using polystyrene.

In the polyurethane polymer of the invention, the number of millimols of phosphorus in the phosphorylcholine structure of the formula (1) per 1.0 g of the polymer (hereinafter abbreviated as "meq/g") is preferably about 0.03 to 3.00 meq/g, more preferably about 0.06 to 2.80 meq/g.

Since phosphorylcholine with a structure analogous to that of phosphatidylcholine forming biomembranes has been introduced to the side chain of the polyurethane polymer of the invention, the polyurethane polymer of the invention has remarkably superior antithrombogenicity to polyurethanes containing phosphorylcholine in the main chain. Further, when a hydrophilic polyoxyalkylene group is introduced to the end of the side chain of the polyurethane polymer, the polyurethane polymer exhibits antithrombogenicity more effectively than when an alkyl group is introduced to the end of the side chain.

Complex with Mucopolysaccharide

Of the polyurethane polymer of the present invention, those having quaternary ammonium group of the formula (4) or (5) in the molecule can form complex with mucopolysaccharide having anticoagulation activity, by the electrostatic interaction.

Mucopolysaccharides useful in the invention include heparin, chondroitin sulfate, hyaluronic acid, dermatan sulfate, keratan sulfate, and their metal salts such as lithium, sodium and potassium salts. Particularly preferred are heparin and its metal salts, which have excellent antithrombogenicity.

The method for preparing the complex of the mucosaccharide and the polyurethane polymer having ammonium group of the formula (4) or (5) is not limited. The complex can be obtained by, for example, immersing the polyurethane polymer of the invention in an aqueous solution or weakly acidic buffer solution (about pH 3–6) of the mucopolysaccharide at about 20 to 100° C. for about 1 to 24 hours. The polyurethane polymer of the invention is preferably made into the complex usually after being formed into a desired article or coating layer. When using the polyurethane polymer of the invention as mixed with another polymer, the mixture may be treated by immersion in the above manner.

Examples of preferred solutes in the buffer solution used for preparing the complex include 2-(N-morphorino) ethanesulfonic acid, pyperazine-1,4-bis(2-ethanesulfonic acid), N-(2-acetoamide-2-amonoethanesulfonic acid, N,N-bis(2-hydroxyethyl)-2-aminoethanesulfonic acid, 3-(N-morpholino)propanesulfonic acid, 3-(N-morpholino)-2-hydroxypropanesulfonic acid, and 2-[4-(2-hydroxyethyl)-1-pyperadinyl]ethanesulfonic acid. Among them, particularly preferred are 2-(N-morpholino)ethanesulfonic acid (hereinafter abbreviated as "MES"), piperazine-1,4-bis(2-ethanesulfonic acid) (hereinafter abbreviated as "PIPES") and 3-(N-morpholino)propanesulfonic acid (hereinafter abbreviated as "MOPS"). However, other solutes may be used. Buffer solutions of these solutes may be used as mixed with an organic solvent miscible with water, such as methanol, ethanol, propanol, isopropanol or like alcohol, tetrahydrofuran, N,N-dimethylformaldehyde, N,N-dimethylacetoamide or the like.

When the polyurethane polymer containing phosphorylcholine structure in the side chain is formed into complex with mucopolysaccharide, the complex exhibits, by the action of the mucopolysaccharide, improved antithrombogenicity particularly at the early stage of contact with constituents of the living body. Further, even after a long-term contact, the complex retains good antithrombogenicity by the effect of highly blood-compatible phosphorylcholine. Accordingly, the material can be obtained which stably exhibits good antithrombogenicity not only the early stage of contact with constituents of the living body but also after a long-term contact.

Antithrombogenic Material

The polyurethane polymer of the invention has excellent biocompatibility, can stably exhibits antithrombogenicity for a prolonged period, and are effectively usable particularly as a material for various products for medical use including medical devices and equipments which are required to have blood compatibility, or as a coating material for these products for medical use. Such use of the polyurethane polymer of the invention can provide medical devices, equipments and the like having blood compatibility and capable of stably exhibiting excellent antithrombogenicity.

Specific examples of products for medical use including medical devices and equipments which are required to have blood compatibility and which can be prepared from or coated with the polyurethane polymer of the invention include hemodialysis membranes, plasmapheresis membranes, adsorbents for waste products in blood, membranes for artificial lungs (partition walls between blood and oxygen), sheet materials for sheet lungs in heart-lung machines, artery balloons, blood bags, catheters, cannulas, shunts, blood circuits and stents.

When using the polyurethane polymer of the invention as a coating material, the polyurethane polymer is usually dissolved in an organic solvent such as THF, HMPA, NMP, NMF, DMF, DMAc, a THF-methanol mixture, a THF-ethanol mixture or a THF-propanol mixture, and the solution is applied to the object to be treated by brush-coating, spray-coating, dip-coating or like method. The coating material may optionally contain, in addition to the polyurethane polymer of the invention, polymer materials conventionally used as materials of various products for medical use which need to be biocompatible, such as polyether urethane, polyurethane, polyurethane urea, polyvinyl chloride, polyester, polypropylene and polyethylene. The concentration of the polyurethane polymer of the invention in the coating material is not limited and may be suitably selected according to the kind of the polyurethane polymer used, within a range in which the polyurethane polymer dissolves in the organic solvent. When the polyurethane polymer of the invention is used as mixed with another polymer, the proportion of the polyurethane polymer is preferably about 1 to 99 wt. %, more preferably about 5 to 80 wt. %, per 100 wt % of the combined amount of the polyurethane polymer of the invention and the other polymer.

After applying the coating material, the organic solvent is removed to obtain a coating layer of the polyurethane polymer of the invention. The organic solvent can be removed by any methods without limitations, but is preferably removed by, for example, drying the coating by heating in an atmosphere of nitrogen, argon, helium or like inert gas at about 20 to 100° C. for about 0.1 to 180 minutes, and then under reduced pressure at about 20 to 100° C. for 0.1 to 36 hours.

The thickness of the coating layer is not limited, but is usually about 0.1 to 100 mm, preferably about 0.5 to 70 μm. The thickness can be easily controlled by changing the polymer concentration in the coating composition and number of times of application.

The material of the products for medical use to be coated with the coating material is not limited, but may be any of the above-mentioned polymer materials conventionally used for medical products.

The polyurethane polymer of the invention, when employed as a material of products for medical use, can be used singly or as mixed with any of the above polymer materials usually used for medical products which need to be biocompatible, according to properties required. When the polyurethane polymer of the invention is used as mixed, the proportion of the polyurethane polymer is preferably about 1 to 60 wt. %, more preferably about 5 to 50 wt. %, per 100 wt. % of the combined amount of the polyurethane polymer of the invention and other polymer.

When preparing products for medical use from the polyurethane polymer of the invention, conventional methods for preparation of desired products can be suitably selected.

Effect of the Invention

The polyurethane polymer of the invention has good biocompatibility and can stably exhibit antithrombogenicity not only at the early stage of contact with constituents of the living body but also after a long-term contact therewith.

When using the polyurethane polymer of the invention as a material of products for medical use including medical devices and equipments which need to be blood-compatible or as a coating material for such products, the obtained medical products have blood compatibility and are capable of stably exhibiting excellent antithrombogenicity.

BEST MODE FOR CARRYING OUT THE INVENTION

Examples are given below to illustrate the present invention in further detail, but they are in no way limitative of the scope of the invention.

PRODUCTION EXAMPLE 1

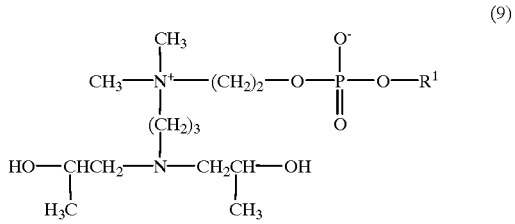

(9)

A diol of the formula (9) wherein $R^1=R^4-(A)_n-$ (wherein $R^4$=butyl, A=an oxyethylene-oxypropylene copolymer and n is 4 on average) (hereinafter abbreviated as "SEO") was prepared by the following method.

A solution of 25.00 g of 2-chloro-2-oxo-1,3,2-dioxaphosphorane (COP) in 150 ml of THF was slowly added dropwise in a nitrogen stream at −20° C. to a solution of 42.00 g of an alcohol of the formula $R^1OH$ wherein $R^1$ is $R^4-(A)_n-$ (wherein $R^4$=butyl, A=an oxyethylene-oxypropylene copolymer and n is 4 on average) [(HO(C_2H_4O)_2 (C_3H_6O)_2C_4H_9$, manufactured by Sanyo Chemical Industries, Ltd. under the trademark "Newpol 50HB-55"] and 24.3 ml of triethylamine in 70 ml of THF. Thereafter, the reaction mixture was stirred in a nitrogen stream at −10° C. for 5 hours. After the reaction, the precipitate (triethylamine hydrochloride) was filtered off, the filtrate was evaporated in vacuo, and the residue was dried in vacuo, giving, as a transparent liquid, a compound of the following formula wherein $R^1=R^4-(A)_n-$ (wherein $R^4$=butyl, A=an oxyethylene-oxypropylene copolymer and n is 4 on average) in a yield of 93%. The compound is hereinafter referred to as "EOOP".

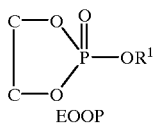

EOOP

Identification of the compound: $^1$H-HMR spectrum (deuterochloroform, 25° C., 200 MHz) δ/ppm: 0.9 (3H, t, CH_3), 1.2 (6H, d, CH_3CHO), 1.3 (2H, m, CH_2Me in Bu), 1.6 (2H, m, OCCH_2), 3.5 (16H, m, OCH_2, (C_2H_4O)_2 (CH_2CHMeO)_2), 4.3 (4H, m, POCH_2).

IR spectrum (neat): 2900, 2840 $(\nu_{CH})$, 1235 $(\nu_{P=O})$, 1050 $(\nu_{C-O-C})$, 1020 $(\nu_{V-PO-C})$ cm$^{-1}$.

Subsequently, equimolar amounts of the obtained EOOP and 4-(3-N,N-dimethylaminopropyl)-4-aza-2,6-dihydroxyheptane (ADO) were dissolved in dry acetonitrile, followed by a reaction in a sealed reactor at 65° C. for 24 hours. After the reaction, the solvent was evaporated in vacuo, and the residue was washed with cyclohexane several times, giving SEO as a yellow viscous liquid in a yield of 87%. Identification of the compound: $^1$H-HMR spectrum (deuterochloroform, 25° C., 200 MHz) δ/ppm: 0.8 (3H, t, $CH_3$ in Bu), 1.1 (6H, d, $CH_3CH$), 1.2 (6H, d, $CH_3CO$), 1.3 (2H, m, $CH_2$ Me in Bu), 1.7 (4H, m, $NCCH_2$, $CH_2Et$ in Bu), 3.2 (6H, s, $NCH_3$), 3.6–4.1 (26H, m, $CH_2CCH_2N$, $N^+CH_2CH_2OP$, $OCH_2$, $(C_2H_4O)_2(CH_2CHMeO)_2)$, 4.3 (2H, m, CHOH). IR spectrum (neat): 3300 ($\nu_{OH}$), 2900 ($\nu_{CH}$), 1200 ($\nu_{P=O}$), 1050 ($\nu_{C-O-C}$), 1040 ($\nu_{-PO-C}$) cm$^{-1}$.

PRODUCTION EXAMPLE 2

A compound of the formula (9) wherein $R^1$=octyl, i.e., 2-[3,7-diaza-3,3-dimethyl-7-(2-hydroxypropyl)-9-hydroxydecyl]-2'-octylphosphate (hereinafter abbreviated as "$SC_8$"), was prepared by the following method.

A solution of 24.10 g of COP in 100 ml of THF was slowly added dropwise to a solution of 26.8 ml of octanol and 23.6 ml of triethylamine in 50 ml of THF, in a nitrogen stream at −200C. After completion of addition, the mixture was reacted in a nitrogen stream at −10° C. for 5 hours. Thereafter, the precipitate (triethylamine hydrochloride) was filtered off, the filtrate was evaporated in vacuo, and the residue was dried in vacuo, giving 2-octyloxy-2-oxo-1,3,2-phosphorane (OOP) as a colorless transparent liquid in a yield of 95%.
Identification of the compound: $^1$H-HMR spectrum (deuterochloroform, 25° C., 200 MHz) δ/ppm: 0.8 (6H, t, $CH_3$), 1.3 (10H, s, $OCC(CH_2)_5$), 1.7 (2H, m, $OCCH_2$), 4.1 (2H, t, $OCH_2$), 4.3 (4H, m, $POCH_2$).
IR spectrum (neat): 2900, 2840 ($\nu_{CH}$), 1235 ($\nu_{P=O}$), 1020 ($\nu_{-PO-C}$) cm$^{-1}$.

Subsequently, equimolar amounts of the obtained OOP and ADO were dissolved in dry acetonitrile, followed by a reaction in a sealed reactor at 65° C. for 24 hours. After the reaction, the solvent was evaporated in vacuo, and the residue was washed with cyclohexane several times, giving $SC_8$ as a yellow viscous liquid in a yield of 93%.
Identification of the compound: $^1$H-HMR spectrum (deuterochloroform, 25° C., 200 MHz) δ/ppm: 0.8 (3H, t, $CH_3$), 1.1 (6H, d, $CH_3CH$), 1.3 (10H, s, $OCC(CH_2)_5$), 1.6 (2H, m, $NCCH_2$), 1.7 (2H, m, $OCCH_2$ in Oct), 3.2 (6H, s, $NCH_3$), 3.6–4.1 (14H, m, $CH_2NCH_2CCH_2N$, $NCH_2CH_2OPOCH_2$), 4.3 (2H, m, CHOH).
IR spectrum (neat): 3300 ($\nu_{OH}$), 2900 ($\nu_{CH}$), 1220 ($\nu_{P=O}$), 1040 ($\nu_{-PO-C}$) cm$^{-1}$.

PRODUCTION EXAMPLE 3

The procedure of Production Example 2 was followed with the exception of using 2-N,N-dimethylaminomethyl-2-methyl-1,3-propanediol in place of ADO, giving 2-(3-aza-3,3-dimethyl-5,5-bishydroxymethyl-hexyl)-2'-octyl phosphate as a yellow viscous liquid in a yield of 89%.
Identification of the compound: $^1$H-HMR spectrum (deuterochloroform, 25° C., 200 MHz) δ/ppm: 0.8 (3H, t, $CH_3$ in Oct), 1.2 (3H, s, $CCH_3$), 1.3 (10H, s, $OCC(CH_2)_5$), 1.7(2H, m, $OCCH_2$) 3.2 (6H, s, $NCH_3$), 3.6–4.1 (12H, m, $CH_2N^+CH_2CH_2OPOCH_2$), 4.3 (2H, m, CHOH).
IR spectrum (neat): 3300 ($\nu_{OH}$), 2900 ($\nu_{CH}$), 1220 ($\nu_{P=O}$), 1040 ($\nu_{-PO-C}$) cm$^{-1}$.

EXAMPLE 1

In 70 ml of DMAc were dissolved 7.90 g of SEO obtained in Production Example 1, 20.28 g of polytetramethylene glycol (average molecular weight 1300, hereinafter abbreviated as "PTMG"), and 3.64 g of butane diol (hereinafter abbreviated as "BD"). After throughly replacing air in the reactor with argon gas, a solution of 18.36 g of 4,4'-methylenebis(cyclohexylisocyanate) (hereinafter abbreviated as "HMDI") in 30 ml of DMAc was slowly added dropwise to the above solution. After the addition, the reaction mixture was stirred at 100° C. for 24 hour to effect polymerization. The resulting reaction mixture was poured into 1500 ml of water with stirring. The precipitate was filtered off, and then it was dissolved in tetrahydrofuran (hereinafter abbreviated as THF). The solution was poured into an aqueous solution of 50 vol % methanol, and the precipitate was collected and dried in vacuo, giving a polymer A. The obtained polymer A had a weight-average molecular weight of 123,000.

The polymer A was dissolved in THF to obtain a 5% solution. 20 g of the obtained solution was uniformly placed on a 12 cm×12 cm glass plate which was kept even, dried in a nitrogen stream at 40° C. for 8 hours, and then at 40° C. under reduced pressure for 15 hours, giving a film A1 having a thickness of about 60 μm.

Using the film, plasma relative coagulation time was determined as follows.

The film A1 was cut into a disc with a diameter of about 3 cm and pasted at the center of a watch glass with a diameter of 10 cm. 200 μl of citrated rabbit (Japanese white rabbit) plasma was placed on the film, and 200 μl of an aqueous solution of 0.025 mol/l of calcium chloride was added to the plasma. The watch glass was floated in an incubator at 37° C. and gently shaken so as to mix the plasma with the solution. The lapse of time from the addition of the aqueous solution of calcium chloride to the coagulation of the plasma (the point when the plasma became still) was measured. The measured value was divided by the time necessary for the plasma coagulation when the same procedure was performed on a glass plate. The obtained value was used as the relative coagulation time.

The polymer A solution was diluted with THF to give a 1% solution. Glass beads (40 to 60 mesh) were immersed in the solution for 30 minutes, collected by filtration through a glass filter, and dried in a nitrogen stream at 40° C. for 8 hours and then in vacuo at 40° C. for 15 hours, giving beads Al coated with the polymer A. 100 mg of the coated beads Al were immersed in 1 ml of a two-fold diluted suspension of human serum with PBS, and incubated at 37° C. for 30 minutes with gently shaking. Using this mixture as a sample, hemolytic unit of complement (CH50) was determined by the Mayer method (Mayer, M. M., "Complement and Complement fixation" Experimental Immunochemistry 2nd Ed. pp. 133–240, C. C. Thomas Publisher, 1961). The result is shown in Table 1 in percentage relative to the hemolytic unit of complement of 1 ml of the above-mentioned diluted serum without the beads.

The film A1 was immersed in PBS to effect elution in an incubator at 37° C. for two weeks, giving a film A2. During the elution, PBS was changed every day. The plasma relative coagulation time of the film A2 was measured in the same manner as described above. The result is shown in Table 1.

A 2% solution of the polymer A in THF was prepared. A known polypropylene porous hollow fiber for artificial lungs was immersed in the solution, taken out therefrom, and dried at 40° C. for 12 hours, giving a hollow fiber A1 coated with the polymer A.

Using the hollow fiber A1, in vivo antithrombogenicity was evaluated as follows.

The femoral vein of a rabbit (Japanese white rabbit, male, 2.5 to 3.0 kg) was detached under pentobarbital anesthesia. The peripheral side thereof was ligated with a yarn, and clamped with a hemostat at a site 2–3 cm away from the yarn. The blood vessel was cut at a more central portion than the ligated portion with scissors to ¼–⅓ of the diameter of the vessel. The sample hollow fiber was inserted from the cut portion toward the central side to a length of 10 cm. At a portion 1 cm away from the insertion site, the end portion of the hollow fiber extending from the blood vessel was sewn to prevent the hollow fiber from being carried away. The incised section was sutured, and an antibiotic was administered. The rabbit was bred for one month until the sample was taken out. One month later, the rabbit underwent median incision under heparinized pentobarbital anesthesia. A suitable tube was inserted into the abdominal aorta for exsanguination to sacrifice the rabbit. Then, the blood vessel into which the hollow fiber had been inserted was sectioned. The blood vessel was incised and the hollow fiber and the inside of the blood vessel were photodocumented, and visually observed for five-rank evaluation. The results are shown in Table 1.

The criteria for the five-rank evaluation of in vivo antithrombogenicity shown in Table 1 are as follows:

a: none of platelet aggregation, thrombus formation and fibrin formation were observed;

b: fibrin formation or platelet aggregation was found, but thrombus formation was not observed;

c: fibrin formation or platelet aggregation was found, and thrombus formation was slightly observed;

d: fibrin formation or platelet aggregation was found, and thrombus formation was found to a considerable extent;

e: fibrin formation or platelet aggregation was found and a large amount of thrombus formed was observed.

EXAMPLE 2

7.901 g of SEO, 13.52 g of PTMG and 4.11 g of BD were dissolved in 70 ml of DMAc. To this solution, a solution of 18.36 g of HMDI in 30 ml of DMAc was added dropwise under the same conditions as in Example 1. The subsequent procedure was carried out in the same manner as in Example 1, giving a polymer B. The polymer B had a weight-average molecular weight of 104,000.

A film B1, coated beads B1 and a hollow fiber B1 were prepared from the polymer B by following the procedure described in Example 1.

The plasma relative coagulation time, hemolytic unit of complement and in vivo antithrombogenicity of these samples were determined in the same manner as in Example 1. The results are shown in Table 1.

Further, the film B1 was subjected to elution with PBS, and the eluted film B2 was tested for plasma relative coagulation time. The result is shown in Table 1.

EXAMPLE 3

In 70 ml of DMAc were dissolved 7.90 g of SEO, 1.88 g of N-{N',N'-bis(2-hydroxypropyl)amino}propylene-N,N-dimethylammonium chloride (hereinafter abbreviated as "ADO-Cl"), 20.80 g of PTMG and 3.97 g of BD. To this solution, a solution of 18.36 g of HMDI in 30 ml of DMAc was added dropwise under the same conditions as in Example 1. The subsequent procedure was carried out in the same manner as in Example 1, giving a polymer C. The obtained polymer C had a weight-average molecular weight of 95,000.

A film C1 was prepared from the polymer C by following the procedure described in Example 1. The plasma relative coagulation time of this sample was determined in the same manner as in Example 1.

The film C1, coated beads C1 and a hollow fiber C1, all prepared from the polymer C by following the procedure described in Example 1, were separately immersed in 200 ml of a 1% heparin sodium solution in PBS at 25° C. for 24 hours, giving a film C2, coated beads C2 and a hollow fiber C2. The plasma relative coagulation time, hemolytic unit of complement and in vivo antithrombogenicity of these samples were determined in the same manner as in Example 1.

Further, the films C1 and C2 were subjected to elution with PBS, giving eluted films C3 and C4, respectively. The obtained films C3 and C4 were tested for plasma relative coagulation time.

The results are shown in Table 1.

EXAMPLE 4

In 70 ml of DMAc were dissolved 7.90 g of SEO, 0.94 g of ADO-Cl, 20.41 g of PTMG and 3.32 g of BD. To this solution, a solution of 18.36 g of HMDI in 30 ml of DMAc was added dropwise under the same conditions as in Example 1. The subsequent procedure was carried out in the same manner as in Example 1, giving a polymer D. The obtained polymer D had a weight-average molecular weight of 76,000.

A film D1 was prepared from the polymer D by following the procedure described in Example 1. The plasma relative coagulation time of this sample was determined in the same manner as in Example 1.

The film D1, coated beads D1 and a hollow fiber D1, all prepared from the polymer D by following the procedure described in Example 1, were separately immersed in 200 ml of a 1% heparin sodium solution in PBS at 25° C. for 24 hours, giving a film D2, coated beads D2 and a hollow fiber D2. The plasma relative coagulation time, hemolytic unit of complement and in vivo antithrombogenicity of these samples were determined in the same manner as in Example 1.

Further, the films D1 and D2 were subjected to elution with PBS, giving eluted films D3 and D4, respectively. The obtained films D3 and D4 were tested for plasma relative coagulation time.

The results are shown in Table 1.

EXAMPLE 5

In 70 ml of DMAc were dissolved 7.90 g of SEO, 0.59 g of N,N-dimethyl-N,N-diethanolammonium chloride (hereinafter abbreviated as "MDEA-Cl"), 20.15 g of PTMG and 3.34 g of BD. To this solution, a solution of 18.36 g of HMDI in 30 ml of DMAC was added dropwise under the same conditions as in Example 1. The subsequent procedure was carried out in the same manner as in Example 1, giving a polymer E. The obtained polymer E had a weight-average molecular weight of 147,000.

A film E1 was prepared from the polymer E by following the procedure described in Example 1. The plasma relative coagulation time of this sample was determined in the same manner as in Example 1.

The film E1, coated beads E1 and a hollow fiber E1, all prepared from the polymer E by following the procedure described in Example 1, were separately immersed in 200 ml of a 1% heparin sodium solution in PBS at 25° C. for 24 hours, giving a film E2, coated beads E2 and a hollow fiber E2. The plasma relative coagulation time, hemolytic unit of complement and in vivo antithrombogenicity of these samples were determined in the same manner as in Example 1.

Further, the films E1 and E2 were subjected to elution with PBS, giving eluted films E3 and E4, respectively. The obtained films F3 and F4 were tested for plasma relative coagulation time.

The results are shown in Table 1.

EXAMPLE 6

In 70 ml of DMAc were dissolved 3.95 g of SEO, 17.81 g of PTMG and 4.44 g of BD. To this solution, a solution of 18.36 g of HMDI in 30 ml of DMAc was added dropwise under the same conditions as in Example 1. The subsequent procedure was carried out in the same manner as in Example 1, giving a polymer F. The obtained polymer F had a weight-average molecular weight of 94,000.

A film F1, coated beads F1 and a hollow fiber F1 were prepared from the polymer F by following the procedure described in Example 1.

The plasma relative coagulation time, hemolytic unit of complement and in vivo antithrombogenicity of these samples were determined in the same manner as in Example 1. The results are shown in Table 1.

Further, the film F1 was subjected to elution with PBS, and the eluted film F2 was tested for plasma relative coagulation time. The result is shown in Table 1.

EXAMPLE 7

In 70 ml of DMAc were dissolved 3.95 g of SEO, 0.94 g of ADO-Cl, 18.20 g of PTMG and 4.10 g of BD. To this solution, a solution of 18.36 g of HMDI in 30 ml of DMAc was added dropwise under the same conditions as in Example 1. The subsequent procedure was carried out in the same manner as in Example 1, giving a polymer G. The obtained polymer G had a weight-average molecular weight of 83,000.

A film G1 was prepared from the polymer G by following the procedure described in Example 1. The plasma relative coagulation time of this sample was determined in the same manner as in Example 1.

The film G1, coated beads G1 and a hollow fiber G1, all prepared from the polymer G by following the procedure descried in Example 1, were separately immersed in 200 ml of a 1% heparin sodium solution in PBS at 25° C. for 24 hours, giving a film G2, coated beads G2 and a hollow fiber G2. The plasma relative coagulation time, hemolytic unit of complement and in vivo antithrombogenicity of these samples were determined in the same manner as in Example 1.

Further, the films G1 and G2 were subjected to elution with PBS, giving eluted films G3 and G4, respectively. The obtained films G3 and G4 were tested for plasma relative coagulation time.

The results are shown in Table 1.

EXAMPLE 8

In 70 ml of DMAc were dissolved 9.55 g of $SC_8$ obtained in Production Example 2, 20.54 g of PTMG and 2.99 g of BD. To this solution, a solution of 18.36 g of HMDI in 30 ml of DMAc was added dropwise under the same conditions as in Example 1. The subsequent procedure was carried out in the same manner as in Example 1, giving a polymer H. The obtained polymer H had a weight-average molecular weight of 132,000.

A film H1, coated beads H1 and a hollow fiber H1 were prepared from the polymer F by following the procedure described in Example 1.

The plasma relative coagulation time, hemolytic unit of complement and in vivo antithrombogenicity of these samples were determined in the same manner as in Example 1. The results are shown in Table 1.

Further, the film H1 was subjected to elution with PBS, and the eluted film H2 was tested for plasma relative coagulation time. The result is shown in Table 1.

EXAMPLE 9

In 70 ml of DMAc were dissolved 9.55 g of $SC_8$, 13.39 g of PTMG and 3.49 g of BD. To this solution, a solution of 18.36 g of HMDI in 30 ml of DMAc was added dropwise under the same conditions as in Example 1. The subsequent procedure was carried out in the same manner as in Example 1 to give a polymer I. The obtained polymer I had a weight-average molecular weight of 68,000.

A film I1, coated beads I1 and a hollow fiber I1 were prepared from the polymer I by following the procedure described in Example 1.

The plasma relative coagulation time, hemolytic unit of complement and in vivo antithrombogenicity of these samples were determined in the same manner as in Example 1. The results are shown in Table 1.

Further, the film I1 was subjected to elution with PBS, and the eluted film I2 was tested for plasma relative coagulation time. The result is shown in Table 1.

EXAMPLE 10

In 70 ml of DMAc were dissolved 9.55 g of $SC_8$, 0.94 g of ADO-Cl, 21.06 g of PTMG and 2.64 g of BD. To this solution, a solution of 18.36 g of HMDI in 30 ml of DMAc was added dropwise under the same conditions as in Example 1. The subsequent procedure was carried out in the same manner as in Example 1, giving a polymer J. The obtained polymer J had a weight-average molecular weight of 88,000.

A film J1 was prepared from the polymer J by following the procedure described in Example 1. The plasma relative coagulation time of this sample was determined in the same manner as in Example 1.

The film J1, coated beads J1 and a hollow fiber J1, all prepared from the polymer J by following the procedure described in Example 1, were separately immersed in 200 ml of a 1% heparin sodium solution in PBS at 25° C. for 24 hours, giving a film J2, coated beads J2 and a hollow fiber J2. The plasma relative coagulation time, hemolytic unit of complement and in vivo antithrombogenicity of these samples were determined in the same manner as in Example 1. The results are shown in Table 1.

Further, the films J1 and J2 were subjected to elution with PBS, giving eluted film J3 and J4, respectively. The obtained films J3 and J4 were tested for plasma relative coagulation time.

The results are shown in Table 1.

EXAMPLE 11

In 70 ml of DMAc were dissolved 3.18 g of $SC_8$, 17.29 g of PTMG and 4.48 g of BD. To this solution, a solution of 18.36 g of HMDI in 30 ml of DMAc was added dropwise under the same conditions as in Example 1. The subsequent procedure was carried out in the same manner as in Example 1, giving a polymer K. The obtained polymer K had a weight-average molecular weight of 114,000.

A film K1, coated beads K1 and a hollow fiber K1 were prepared from the polymer K by following the procedure described in Example 1.

The plasma relative coagulation time, hemolytic unit of complement and in vivo antithrombogenicity of these samples were determined in the same manner as in Example 1. The results are shown in Table 1.

Further, the film K1 was subjected to elution with PBS, and the eluted film K2 was tested for plasma relative coagulation time. The result is shown in Table 1.

EXAMPLE 12

In 70 ml of DMAc were dissolved 3.18 g of $SC_8$, 0.94 g of ADO-Cl, 17.68 g of PTMG and 4.14 g of BD. To this solution, a solution of 18.36 g of HMDI in 30 ml of DMAc was added dropwise under the same conditions as in Example 1. The subsequent procedure was carried out in the same manner as in Example 1, giving a polymer L. The obtained polymer L had a weight-average molecular weight of 165,000.

A film L1 was prepared from the polymer L by following the procedure described in Example 1. The plasma relative coagulation time of this sample was determined in the same manner as in Example 1.

The film Li, coated beads L1 and a hollow fiber L1, all prepared from the polymer L by following the procedure described in Example 1, were separately immersed in 200 ml of a 1% heparin sodium solution in PBS at 25° C. for 24 hours, giving a film L2, coated beads L2 and a hollow fiber L2. The plasma relative coagulation time, hemolytic unit of complement and in vivo antithrombogenicity of these samples were determined in the same manner as in Example 1.

Further, the films L1 and L2 were subjected to elution with PBS, giving eluted films L3 and L4, respectively. The obtained films were tested for plasma relative coagulation time.

The results are shown in Table 1.

COMPARATIVE EXAMPLE 1

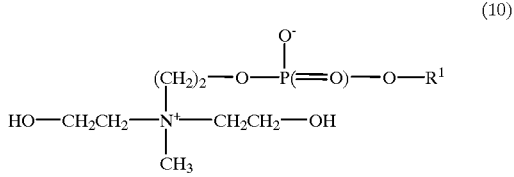

(10)

In 70 ml of DMAc were dissolved 7.46 g of a compound of the formula (10) wherein $R^1$=octyl, i.e., 2-[bis(2-hydroxyethyl)methylammonio]ethyl-2'-octylphosphate (hereinafter abbreviated as "$MC_8$"), 19.24 g of PTMG and 3.08 g of BD. To the solution, a solution of 18.36 g of HMDI in 30 ml of DMAc was added dropwise under the same conditions as in Example 1. The subsequent procedure was carried out in the same manner as in Example 1, giving a polymer M. The obtained polymer M had a weight-average molecular weight of 89,000.

A film M1, coated beads M1 and a hollow fiber M1 were prepared from the polymer M by following the procedure described in Example 1.

The plasma relative coagulation time, hemolytic unit of complement and in vivo antithrombogenicity of these samples were determined in the same manner as in Example 1. The results are shown in Table 1.

Further, the film M1 was subjected to elution with PBS, and the eluted film M2 was tested for plasma relative coagulation time. The result is shown in Table 1.

COMPARATIVE EXAMPLE 2

In 70 ml of DMAc were dissolved 7.46 g of $MC_8$, 0.59 g of MDEA-Cl, 19.50 g of PTMG and 2.75 g of BD. To this solution, a solution of 18.36 g of HMDI in 30 ml of DMAc was added dropwise under the same conditions as in Example 1. The subsequent procedure was carried out in the same manner as in Example 1, giving a polymer N. The obtained polymer N had a weight-average molecular weight of 79,000.

A film N1 was prepared from the polymer N by following the procedure described in Example 1. The plasma relative coagulation time of this sample was determined in the same manner as in Example 1.

The film N1, coated beads N1 and a hollow fiber N1, all prepared from the polymer N by following the procedure described in Example 1, were separately immersed in 200 ml of a 1% heparin sodium solution in PBS at 25° C. for 24 hours, giving a film N2, coated beads N2 and a hollow fiber N2. The plasma relative coagulation time, hemolytic unit of complement and in vivo antithrombogenicity of these samples were determined in the same manner as in Example 1.

Further, the films N1 and N2 were subjected to elution with PBS, giving eluted films N3 and N4, respectively. The obtained films N3 and N4 were tested for plasma relative coagulation time.

The results are shown in Table 1.

COMPARATIVE EXAMPLE 3

In 70 ml of DMAc were dissolved 2.49 g of $MC_8$, 16.90 g of PTMG and 4.51 g of BD. To the solution, a solution of 18.36 g of HMD in 30 ml of DMAc was added dropwise under the same conditions as in Example 1. The subsequent procedure was carried out in the same manner as in Example 1, giving a polymer O. The obtained polymer O had a weight-average molecular weight of 152,000.

A film O1, coated beads O1 and a hollow fiber O1 were prepared from the polymer O by following the procedure described in Example 1.

The plasma relative coagulation time, hemolytic unit of complement and in vivo antithrombogenicity of these samples were determined in the same manner as in Example 1. The results are shown in Table 1.

Further, the film O1 was subjected to elution with PBS, and the eluted film O2 was tested for plasma relative coagulation time. The result is shown in Table 1.

COMPARATIVE EXAMPLE 4

In 70 ml of DMAc were dissolved 2.49 g of $MC_8$, 0.59 g of MDEA-Cl, 17.03 g of PTMG and 4.18 g of BD. To this solution, a solution of 18.36 g of HMDI in 30 ml of DMAc was added dropwise under the same conditions as in Example 1. The subsequent procedure was carried out in the same manner as in Example 1, giving a polymer P. The obtained polymer P had a weight-average molecular weight of 102,000.

A film P1 was prepared from the polymer P by following the procedure described in Example 1. The plasma relative coagulation time of this sample was determined in the same manner as in Example 1.

The film P1, coated beads P1 and a hollow fiber P1, all prepared from the polymer P by following the procedure described in Example 1, were separately immersed in 200 ml of a 1% heparin sodium solution in PBS at 25° C. for 24 hours, giving a film P2, coated beads P2 and a hollow fiber P2. The plasma relative coagulation time, hemolytic unit of complement and in vivo antithrombogenicity of these samples were determined in the same manner as in Example 1.

Further, the films P1 and P2 were subjected to elution with PBS, giving eluted films P3 and P4, respectively. The obtained films P3 and P4 were tested for plasma relative coagulation time.

The results are shown in Table 1.

COMPARATIVE EXAMPLE 5

Following the procedure described in Example 1, a film Q1, coated beads Q1 and a hollow fiber Q1 were prepared from a commercially available polyurethane "Tecoflex" (product of Thermedics) which are widely used as a medical material.

The plasma relative coagulation time, hemolytic unit of complement and in vivo antithrombogenicity of these samples were determined in the same manner as in Example 1. The results are shown in Table 1.

Further, the film Q1 was subjected to elution with PBS, and the eluted film Q2 was tested for plasma relative coagulation time. The result is shown in Table 1.

TABLE 1

| Sample No. | | Relative coagulation time (coagulation time on glass = 1.00) | in vivo antithrombogenicity | Hemolytic unit of complement (%) |
|---|---|---|---|---|
| Ex. No. | | | | |
| 1 | A1 | 7.2 | a | 80 |
| | A2 | 7.0 | — | — |
| 2 | B1 | 7.1 | a | 81 |
| | B2 | 6.8 | — | — |
| 3 | C1 | 7.2 | — | — |
| | C2 | >10 | a | 88 |
| | C3 | 7.0 | — | — |
| | C4 | 7.1 | — | — |
| 4 | D1 | 7.1 | — | — |
| | D2 | >10 | a | 88 |
| | D3 | 7.0 | — | — |
| | D4 | 6.9 | — | — |
| 5 | E1 | 7.1 | — | — |
| | E2 | >10 | a | 85 |
| | E3 | 6.9 | — | — |
| | E4 | 6.9 | — | — |
| 6 | F1 | 6.2 | b | 76 |
| | F2 | 5.9 | — | — |
| 7 | G1 | 5.9 | — | — |
| | G2 | >10 | b | 79 |
| | G3 | 5.8 | — | — |
| | G4 | 5.8 | — | — |
| 8 | H1 | 6.2 | b | 73 |
| | H2 | 6.1 | — | — |
| 9 | I1 | 6.1 | — | — |
| | I2 | 5.8 | b | 72 |
| 10 | J1 | 6.0 | — | — |
| | J2 | >10 | b | 78 |
| | J3 | 5.7 | — | — |
| | J4 | 5.7 | — | — |

TABLE 1-continued

| Sample No. | | Relative coagulation time (coagulation time on glass = 1.00) | in vivo antithrombogenicity | Hemolytic unit of complement (%) |
|---|---|---|---|---|
| 11 | K1 | 4.0 | c | 70 |
| | K2 | 3.8 | — | — |
| 12 | L1 | 3.9 | — | — |
| | L2 | >10 | c | 85 |
| | L3 | 3.7 | — | — |
| | L4 | 3.6 | — | — |
| Comp. Ex. No. | | | | |
| 1 | M1 | 3.2 | c | 69 |
| | M2 | 2.9 | — | — |
| 2 | N1 | 3.2 | — | — |
| | N2 | >10 | c | 70 |
| | N3 | 2.7 | — | — |
| | N4 | 2.7 | — | — |
| 3 | O1 | 2.8 | d | 68 |
| | O2 | 2.7 | — | — |
| 4 | P1 | 2.9 | — | — |
| | P2 | >10 | d | 67 |
| | P3 | 2.6 | — | — |
| | P4 | 2.6 | — | — |
| 5 | Q1 | 1.9 | e | 60 |
| | Q2 | 2.0 | — | — |

As is evident from the results shown in Table 1, the films formed from the polyurethane polymers of the present invention show excellent antithrombogenicity and retain the ability even after indwelling in a blood vessel for one month.

Comparing Example 1 with Example 6, and Example 8 with Example 11, there are differences in antithrombogenicity because of the differences in phosphorylcholine contents in the polymers. In addition, the materials obtained in Comparative Examples 1 to 4, which contain phosphorylcholine in the main chain, not in the side chain, have higher antithrombogenicity than the material of Comparative Example 5, due to the presence of phosphorylcholine in their structure. The above two facts reveal that phosphorylcholine closely relates to antithrombogenicity of the materials. Comparing Examples 1 to 12 with Comparative Examples 1 to 4, it is clear that the polymers containing phosphorylcholine in the side chain have much more improved antithrombogenicity than those containing phosphorylcholine in the main chain. It is assumed that phosphorylcholine, when contained in the side chain, can exhibit its properties more efficiently than when contained in the main chain, since the properties are not suppressed by the high-molecular chain. Further, comparing the polymers of Examples 1 to 7 wherein $R^1$ in the formula (9) is a polyoxyalkylene monoalkyl ether group, with the polymers of Examples 8 to 12 wherein $R^1$ in the formula (9) is alkyl, the polymers of Example 1 to 5 have a lower phosphorylcholine derivative content but have higher antithrombogenicity than the polymer of Example 8. This result can be achieved presumably due to the presence of a hydrophilic group, i.e., polyoxyalkylene, which improves the antithrombogenicity.

Further, as is clear from Examples 3 to 5, when heparin is introduced into polymers containing quaternary ammonium cation, the resulting polymers exhibit significantly improved antithrombogenicity at the early stage. However, when these polymers are subjected to elution with PBS at 37° C. for two weeks, their antithrombogenicity reduces to the same level as of the polymers without heparin. This fact indicates that the heparin introduced into the polymers is released into PBS, and the polymer loses the effect of heparin. However, the polymers from which heparin has been released retain the same level of antithrombogenicity as of the polymers without heparin, probably because of the effect of phosphorylcholine. In addition, there is no difference in antithrombogenicity of polymers of Examples 3 and 4, in spite of the difference in content of the quaternary ammonium cation which causes electrostatic interaction with heparin. This fact reveals that even a small amount of quaternary ammonium cation is sufficient to form a complex with heparin, and to improve the antithrombogenicity at the early stage. Similar results were obtained in the Comparative Examples, indicating that the effect of heparin is shown only for a short period at the early stage of contact with blood.

The polymers of Examples 1 and 2 are different from each other in soft segment (PTMG) content. The results of these Examples show that the soft segment content does not affect the antithrombogenicity.

These results of Examples and Comparative Examples demonstrate that the polyurethane polymer of the present invention, due to the presence of phosphorylcholine structures in the side chain, stably exhibits antithrombogenicity even after two-week elution with PBS or after one-month indwelling in a rabbit femoral vein. In particular, when a hydrophilic polyoxyalkylene group is introduced to the end of the side chain of the polyurethane polymer of the invention, the polyoxyalkylene group makes the polyurethane polymer hydrophilic, resulting in remarkably excellent antithrombogenicity.

We claim:

1. A biocompatible polyurethane or polyurethane urea having side chains which comprise a phosphorylcholine structure represented by the formula (1):

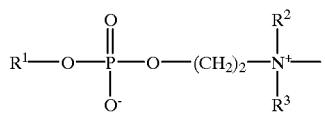

(1)

wherein $R^1$ is $C_{1-20}$ alkyl, $C_{6-12}$ aryl, $C_{7-20}$ aralkyl, or a group of the formula:

wherein A is $C_{2-10}$ oxyalkylene, and $(A)_n$ is constituted of one kind of oxyalkylene groups or of two or more kinds of oxyalkylene groups linked together in blocks or at random; n is an integer of 1 to 30; and $R^4$ is $C_{1-20}$ alkyl, $C_{6-12}$ aryl or $C_{7-20}$ aralkyl; and $R^2$ and $R^3$ each represent $C_{1-20}$ alkyl, $C_{6-12}$ aryl or $C_{7-20}$ aralyky, and are the same or different.

2. A polyurethane or polyurethane urea according to claim 1 containing, per 1.0 g of the polymer, 0.03 to 3.00 mmol of phosphorus in the phosphorylcholine structure of the formula (1).

3. A polyurethane or polyurethane urea according to claim 1 obtained by reacting:

(A) active hydrogen-containing compounds, which are:

(i) 0.1 to 50 mol % of at least one diol containing a phosphorylcholine structure selected from the compounds represented by the formulas (2) and (3):

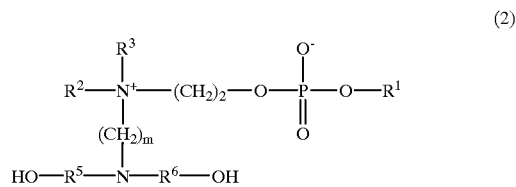

(2)

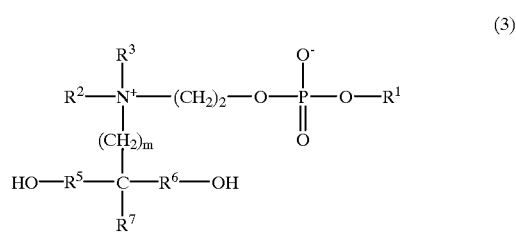

(3)

wherein $R^1$ is $C_{1-20}$ alkyl, $C_{6-12}$ aryl, $C_{7-20}$ aralkyl or a group of the formula:

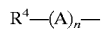

wherein A is $C_{2-10}$ oxyalkylene, and $(A)_n$ is constituted of one kind of oxyalkylene groups or of two or more kinds of oxyalkylene groups linked together in blocks or at random; n in an integer of 1 to 30; and $R^4$ is $C_{1-20}$ alkyl, $C_{6-12}$ aryl or $C_{7-20}$ aralkyl; $R^2$ and $R^3$ each represent $C_{1-20}$ alkyl, $C_{6-12}$ aryl or $C_{7-20}$ aralkyl and are the same or different; $R^5$ and $R^6$ each represent $C_{1-10}$ alkylene and are the same or different; m is an integer of 1 to 10; and $R^7$ in the formula (3) is a hydrogen atom, $C_{1-20}$ alkyl, $C_{6-12}$ aryl or $C_{7-20}$ aralkyl;

(ii) 1 to 40 mol % of at least one polymer diol selected from the group consisting of polyoxyalkylene glycol, polycarbonate diol, polyester diol, polybutadiene diol, polyisoprene diol and hydrogenated polyisoprene diol;

(iii) 1 to 90 mol % of at least one chain extender selected from the group consisting of alkylenediols and alkylenediamines; and (iv) 30 mol % or less of other active hydrogen containing compound; the combined amount of the compounds (i) to (iv) being 100 mol %; with (B) a diisocyanate compound.

4. A polyurethane or polyurethane urea according to claim 3 wherein the diol containing phosphorylcholine structure represented by the formula (1) is at least one member selected from the compounds represented by the formulas (2) and (3):

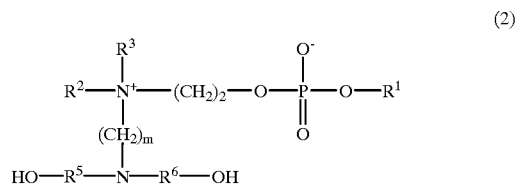

(2)

-continued

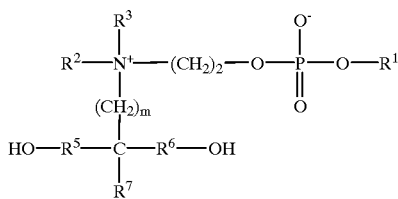
(3)

wherein $R^1$ is $C_{1-20}$ alky, $C_{6-12}$ aryl, $C_{7-20}$ aralkyl or a group of the formula:

$$R^4-(A)_n-$$

wherein A is $C_{2-10}$ oxyalkylene, and $(A)_n$ are constituted of one kind of oxyalkylene groups or of two or more kinds of oxyalkylene groups linked together in blocks or at a random; n is an integer of 1 to 30; and $R^4$ is $C_{1-20}$ alkyl, $C_{6-12}$ aryl or $C_{7-20}$ aralkyl; $R^2$ and $R^3$ each represent $C_{1-20}$ alkyl, $C_{6-12}$ aryl or $C_{7-20}$ aralkyl and are the the same or different; $R^5$ and $R^6$ each represent $C_{2-10}$ alkylene and are the same or different; m is an integer of 1 to 10; and $R^7$ in the formula (3) is a hydrogen atom, $C_{1-20}$ alkyl, $C_{6-12}$ aryl or $C_{7-20}$ aralkyl.

5. A polyurethane or polyurethane urea according to claim 1 claim 3, wherein at least one member selected from the diols containing quaternary ammonium group and represented by the formulas (6) to (8) is used as part or whole of (iv) the other active hydrogen-containing compound, the proportion of the diol being 0.1 mol % or more per 100 mol % of the combined amount of the active hydrogen-containing compounds:

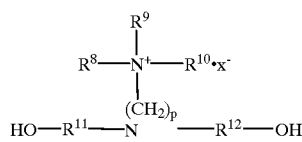
(6)

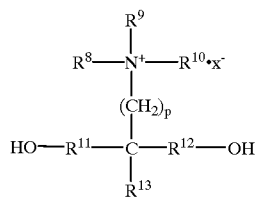
(7)

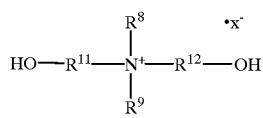
(8)

wherein $R^8$, $R^9$ and $R^{10}$ each represent $C_{1-20}$ alkyl, $C_{6-12}$ aryl or $C_{7-20}$ aralkyl and are the same or different, and any one of $R^8$, $R^9$ and $R^{10}$ is optionally a hydrogen atom; x is an anionic group or an anionic compound; $R^{11}$ and $R^{12}$ each represent $C_{2-10}$ alkylene and are the same or different; $R^{13}$ is $C_{1-20}$ alkyl, $C_{6-12}$ aryl or $C_{7-20}$ aralkyl; and p is an integer of 2 to 10.

6. A polyurethane or polyurethane urea according to claim 1, wherein the side chain further comprises a quaternary ammonium group represented by the formula (4):

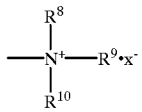
(4)

wherein $R^8$, $R^9$ and $R^{10}$ each represent $C_{1-20}$ alkyl, $C_{6-12}$ aryl or $C_{7-20}$ aralkyl and are the same or different, and any one of $R^8$, $R^9$ and $R^{10}$ is optionally a hydrogen atom; and x is an anionic group or an anionic compound.

7. A polyurethane or polyurethane urea according to claim 1, wherein the main chain comprises a quaternary ammonium group represented by the formula (5):

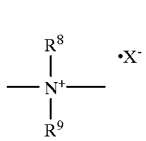
(5)

wherein $R^8$ and $R^9$ each represent $C_{1-20}$ alkyl, $C_{6-12}$ aryl or $C_{7-20}$ aralkyl and are the same or different, and either one of $R^8$ and $R^9$ is optionally a hydrogen atom; and x is an anionic group or an anionic compound.

8. A polyurethane or polyurethane urea according to claim 1 having a weight-average molecular weight of 3,000 to 8,000,000.

9. A polyurethane or polyurethane urea according to claim 6 wherein at least part of ammonium groups forms ionic complex with mucopolysaccharide.

10. A polyurethane or polyurethane urea according to claim 9 wherein the mucopolysacharide is heparin.

11. An antithrombogenic coating material containing a polyurethane or polyurethane urea according to claim 1, as dissolved in an organic solvent.

12. An antithrombogenic material for medical products containing a polyurethane or polyurethane urea according to claim 1 as an active ingredient.

13. An antithrombogenic medical product having a coating layer formed from an antithrombogenic material according to claim 11.

14. An antithrombogenic medical product prepared using an antithrombogenic material according to claim 12.

* * * * *